United States Patent
Wilson et al.

(10) Patent No.: US 11,910,167 B2
(45) Date of Patent: *Feb. 20, 2024

(54) HEARING PROTECTION CALIBRATION ADAPTER DEVICE

(71) Applicant: RAE Systems Inc., Sunnyvale, CA (US)

(72) Inventors: May Bridget Wilson, Charlotte, NC (US); Claes Ingemar Haglund, Charlotte, NC (US); Wei Sun, Charlotte, NC (US); Lei Jiang, Charlotte, NC (US); Huaqing Liao, Charlotte, NC (US)

(73) Assignee: HONEYWELL SAFETY PRODUCTS USA, INC., Charlotte, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/058,512

(22) Filed: Nov. 23, 2022

(65) Prior Publication Data
US 2023/0086797 A1 Mar. 23, 2023

Related U.S. Application Data

(63) Continuation of application No. 17/303,452, filed on May 28, 2021, now Pat. No. 11,540,071.

(30) Foreign Application Priority Data

Jun. 4, 2020 (CN) .......................... 202010499388.X

(51) Int. Cl.
| | |
|---|---|
| *H04R 29/00* | (2006.01) |
| *H04R 1/02* | (2006.01) |
| *H04R 31/00* | (2006.01) |

(52) U.S. Cl.
CPC .............. *H04R 29/00* (2013.01); *H04R 1/02* (2013.01); *H04R 31/00* (2013.01); *H04R 2460/17* (2013.01)

(58) Field of Classification Search
CPC .......... H04R 29/00; H04R 1/02; H04R 31/00; H04R 2460/17

(Continued)

(56) References Cited

U.S. PATENT DOCUMENTS

| | | |
|---|---|---|
| 7,003,128 B2 | 2/2006 | Boonen |
| 8,213,626 B2 | 7/2012 | Weidner |

(Continued)

FOREIGN PATENT DOCUMENTS

| | | |
|---|---|---|
| EP | 3529997 A1 | 8/2019 |
| WO | 2018/075715 A1 | 4/2018 |

(Continued)

OTHER PUBLICATIONS

Binaural Headphone Test Fixture, Model No. AEC206 (Larson Davis, Provo, Utah, United States). Retrieved from http://www.larsondavis.com/Products/ headphone-test-fixtures/research-dev-AEC206 on Sep. 16, 2021.

(Continued)

*Primary Examiner* — Ammar T Hamid
(74) *Attorney, Agent, or Firm* — ALSTON & BIRD LLP

(57) ABSTRACT

A calibration device and method of manufacturing the same. The calibration device for a hearing earpiece configured to at least partially protrude into the ear canal of a user includes a calibration base. The calibration base a calibration insert. An air chamber is defined between the calibration base and the calibration insert. The calibration device also includes at least one earpiece receiving mechanism defined on the calibration insert. The at least one earpiece receiving mechanism is configured to create an sealed connection between given ear piece and the air chamber for calibration. The earpiece receiving mechanism is configured to at least partially receive the given earpiece. A corresponding method of manufacturing is also included.

22 Claims, 10 Drawing Sheets

(58) Field of Classification Search
USPC .................................................. 381/58, 59
See application file for complete search history.

(56) References Cited

U.S. PATENT DOCUMENTS

| | | | |
|---|---|---|---|
| 11,540,071 B2 * | 12/2022 | Wilson .................. | H04R 29/00 |
| 2009/0116656 A1 | 5/2009 | Lee et al. | |
| 2012/0300952 A1 * | 11/2012 | Burnett ................ | H04R 29/004 |
| | | | 381/59 |
| 2014/0146973 A1 | 5/2014 | Liu et al. | |

FOREIGN PATENT DOCUMENTS

| | | | | |
|---|---|---|---|---|
| WO | 2019/092624 A1 | 5/2019 | | |
| WO | WO-2019092624 A1 * | 5/2019 | ........... | H04R 1/1016 |

OTHER PUBLICATIONS

European Search Report dated Nov. 10, 2021 for EP Application No. 21176747, 10 page(s).
Non-Final Office Action dated Apr. 27, 2022 for U.S. Appl. No. 17/303,452.
Notice of Allowance and Fees Due (PTOL-85) dated Aug. 25, 2022 for U.S. Appl. No. 17/303,452.
U.S. Appl. No. 17/303,452, filed May 28, 2021, U.S. Pat. No. 11,540,071, Issued.
EP Office Action dated Sep. 4, 2023 for EP Application No. 21176747, 5 page(s).

* cited by examiner

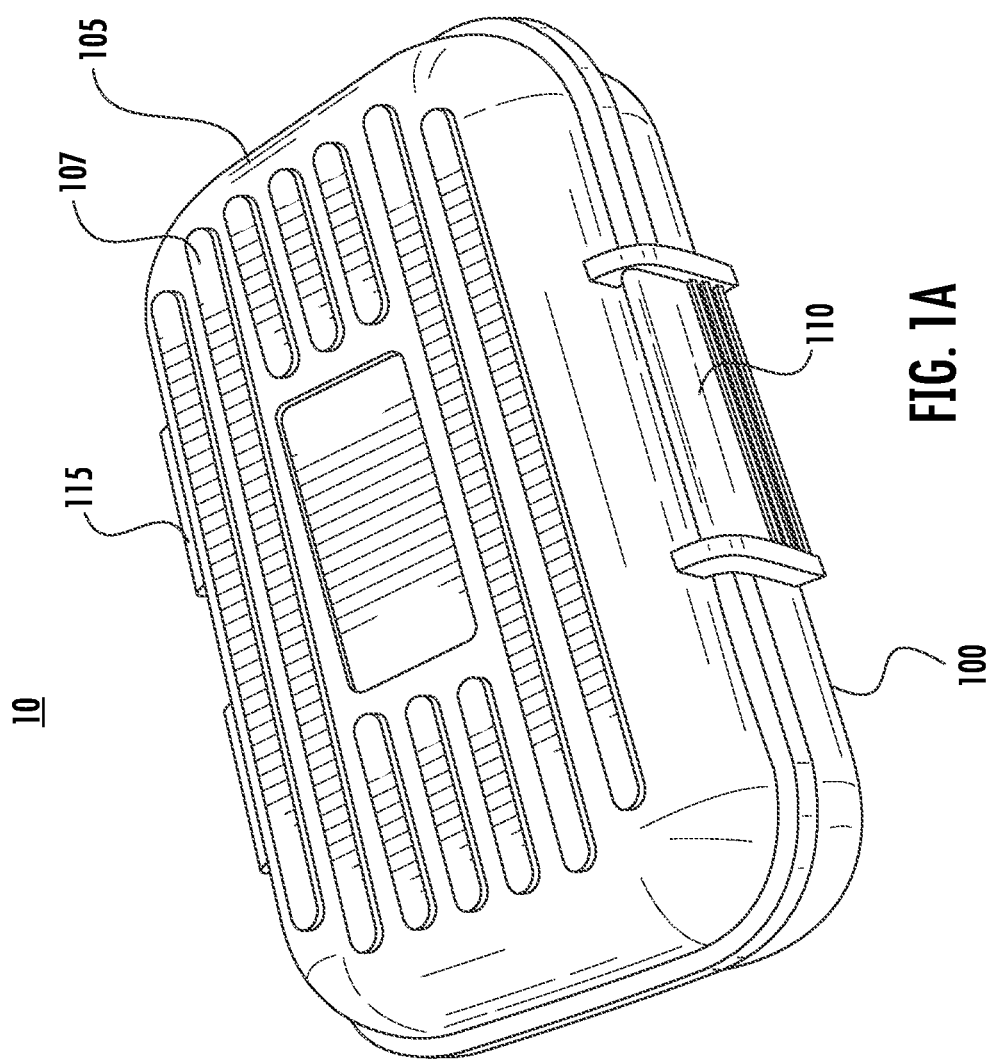

HEARING PROTECTION CALIBRATION ADAPTER DEVICE

CROSS-REFERENCE TO RELATED APPLICATIONS

This application is a continuation of U.S. application Ser. No. 17/303,452, filed May 28, 2021, which claims priority pursuant to 35 U.S.C. 119(a) of China Patent Application No. 202010499388.X, filed Jun. 4, 2020, which application is incorporated herein by reference in its entirety.

TECHNOLOGICAL FIELD

An example embodiment relates generally to the calibration of a hearing protection headset and, more particularly, to portable calibration adapter device for hearing calibration.

BACKGROUND

Hearing devices with noise monitoring functionality used for industrial applications often require periodic calibration to ensure hearing device longevity and accuracy. Applicant has identified a number of deficiencies and problems associated with current hearing devices. Through applied effort, ingenuity, and innovation, many of these identified problems have been solved by the methods and apparatus of the present disclosure.

BRIEF SUMMARY

The following presents a simplified summary in order to provide a basic understanding of some aspects of the present disclosure. This summary is not an extensive overview and is intended to neither identify key or critical elements nor delineate the scope of such elements. Its purpose is to present some concepts of the described features in a simplified form as a prelude to the more detailed description that is presented later.

In an example embodiment, a calibration device for a hearing earpiece is provided. The hearing earpiece is configured to at least partially protrude into the ear canal of a user. The calibration device includes a calibration base comprising a calibration insert. An air chamber is defined between the calibration base and the calibration insert. The calibration device also includes at least one earpiece receiving mechanism defined on the calibration insert. The at least one earpiece receiving mechanism is configured to create a sealed connection between given ear piece and the air chamber for calibration. The earpiece receiving mechanism is configured to at least partially receive the given earpiece.

In some embodiments, the calibration device also includes a calibration tubing receiver configured to operably couple the air chamber with a calibrator system. The calibration system provides calibration to the given ear pieces held in the at least one earpiece receiving mechanism. In some embodiments, each of the least one earpiece receiving mechanism includes one or more microphone seals configured to engage with the given ear piece such that an airtight seal is achieved between the microphone seal and the given ear piece microphone. In some embodiments, each of the earpiece receiving mechanisms includes a tensioning component. The tensioning component is configured to hold the ear piece in the earpiece receiving mechanism during calibration. In some embodiments, the tensioning component is spring loaded. In some embodiments, the calibration device also includes a ejector mechanism. The ejector mechanism is configured to allow an earpiece to be ejected from the calibration insert.

In some embodiments, the earpiece receiving mechanism includes a stationary block and a tensioning component. In such an embodiment, the tensioning component is spring loaded, such that the earpiece is held in place during operation between the stationary block and the tensioning component. In some embodiments, the stationary block includes a microphone seal. The microphone seal is configured to seal one of the microphones of the given earpiece in an instance the given earpiece is positioned between the stationary block and the tensioning component. In some embodiments, an interior microphone seal is positioned on calibration device between the stationary block and the tensioning component. In such embodiments, the interior microphone is configured to seal another microphone of the earpiece in an instance in which the given earpiece is positioned between the stationary block and the tensioning component.

In some embodiments, the at least one earpiece receiving mechanism includes a first earpiece receiving mechanism and a second earpiece receiving mechanism. In such embodiments, the first earpiece receiving mechanism is configured to receive a right ear earpiece and the second earpiece receiving mechanism is configured to receive a left ear earpiece. In some embodiments, the calibration device also includes a calibration tubing configured to be removably attached to the tubing receiver at a first end and the calibrator system at a second end opposite the first end. In some embodiments, the calibration device also includes a lid. The lid is configured to be removably coupled to the calibration base at a locking end of the calibration base and operably coupled to the calibration base at a connection end opposite the lock end, and the lid is configured to move between an opened position and a closed position. In some embodiments, the lid includes one or more calibration tubing hooks configured to hold the calibration tubing in place in an instance the calibration tubing is out of use.

In another example embodiment, a method of manufacturing a calibration device for a hearing earpiece configured to at least partially protrude into the ear canal of a user is provided. The method includes providing a calibration base comprising a calibration insert. An air chamber is defined between the calibration base and the calibration insert. The method also includes providing at least one earpiece receiving mechanism defined on the calibration insert. The at least one earpiece receiving mechanism is configured to create an sealed connection between given ear piece and the air chamber for calibration. The earpiece receiving mechanism is configured to at least partially receive the given earpiece.

In some embodiments, the method also includes providing a calibration tubing receiver configured to operably couple the air chamber with a calibrator system. In such an embodiment, the calibration system provides calibration to the given ear pieces held in the at least one earpiece receiving mechanism. In some embodiments, each of the least one earpiece receiving mechanism includes one or more microphone seals configured to engage with the given ear piece such that an airtight seal is achieved between the microphone seal and the given ear piece microphone. In some embodiments, each of the earpiece receiving mechanisms includes a tensioning component. The tensioning component is configured to hold the ear piece in the earpiece receiving mechanism during calibration. In some embodiments, the tensioning component is spring loaded.

In some embodiments, the method also includes providing a ejector mechanism. In such an embodiment, the ejector mechanism is configured to allow an earpiece to be ejected from the calibration insert. In some embodiments, the earpiece receiving mechanism includes a stationary block and a tensioning component. In such an embodiment, the tensioning component is spring loaded, such that the earpiece is held in place during operation between the stationary block and the tensioning component. In some embodiments, the stationary block includes a microphone seal. The microphone seal is configured to seal one of the microphones of the given earpiece in an instance the given earpiece is positioned between the stationary block and the tensioning component. In some embodiments, an interior microphone seal is positioned on calibration device between the stationary block and the tensioning component. In such an embodiment, the interior microphone is configured to seal another microphone of the earpiece in an instance in which the given earpiece is positioned between the stationary block and the tensioning component.

In some embodiments, the at least one earpiece receiving mechanism includes a first earpiece receiving mechanism and a second earpiece receiving mechanism. In such an embodiment, the first earpiece receiving mechanism is configured to receive a right ear earpiece and the second earpiece receiving mechanism is configured to receive a left ear earpiece. In some embodiments, the method also includes providing a calibration tubing configured to be removably attached to the tubing receiver at a first end and the calibrator system at a second end opposite the first end. In some embodiments, the method also includes operably coupling a lid to the calibration base. The lid is configured to be removably coupled to the calibration base at a locking end of the calibration base and operably coupled to the calibration base at a connection end opposite the lock end, and the lid is configured to move between an opened position and a closed position. In some embodiments, the lid includes one or more calibration tubing hooks configured to hold the calibration tubing in place in an instance the calibration tubing is out of use.

The above summary is provided merely for purposes of summarizing some example embodiments to provide a basic understanding of some aspects of the disclosure. Accordingly, it will be appreciated that the above-described embodiments are merely examples and should not be construed to narrow the scope or spirit of the disclosure in any way. It will be appreciated that the scope of the disclosure encompasses many potential embodiments in addition to those here summarized, some of which will be further described below.

BRIEF DESCRIPTION OF THE DRAWINGS

Figure 1B:
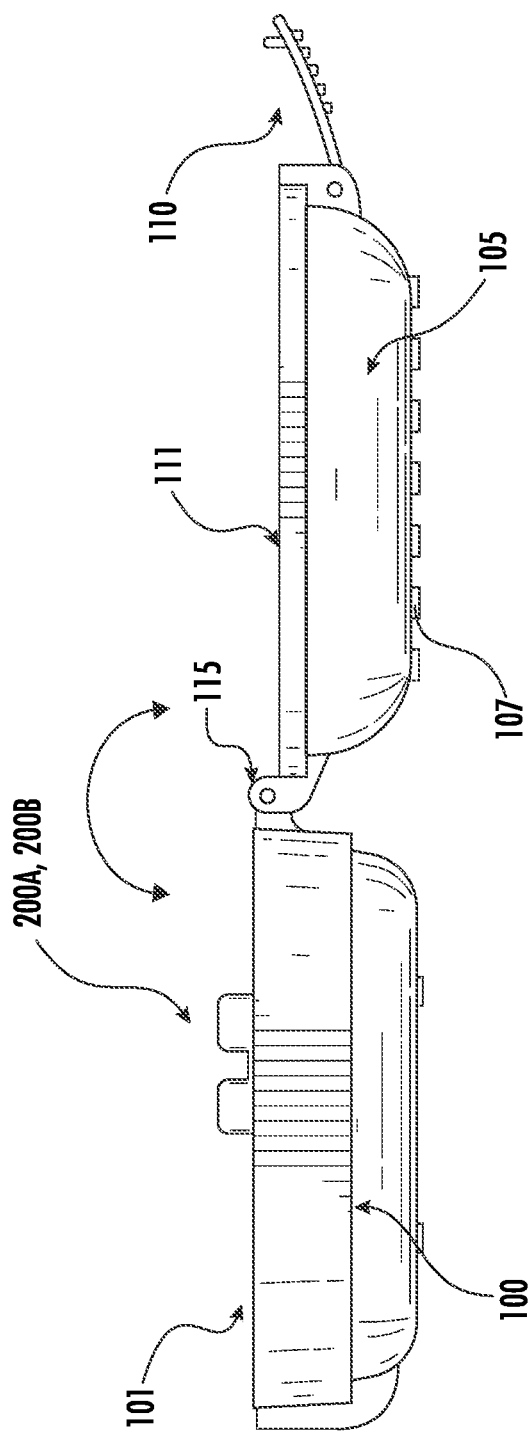
Figure 2A:
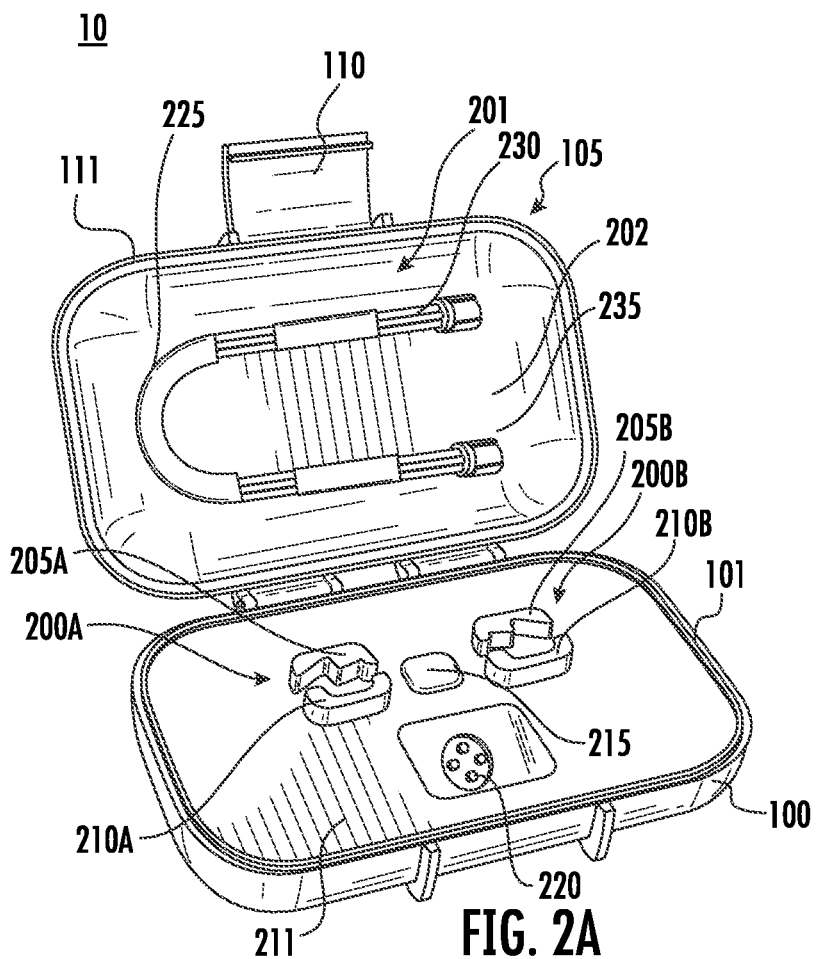
Figure 2B:
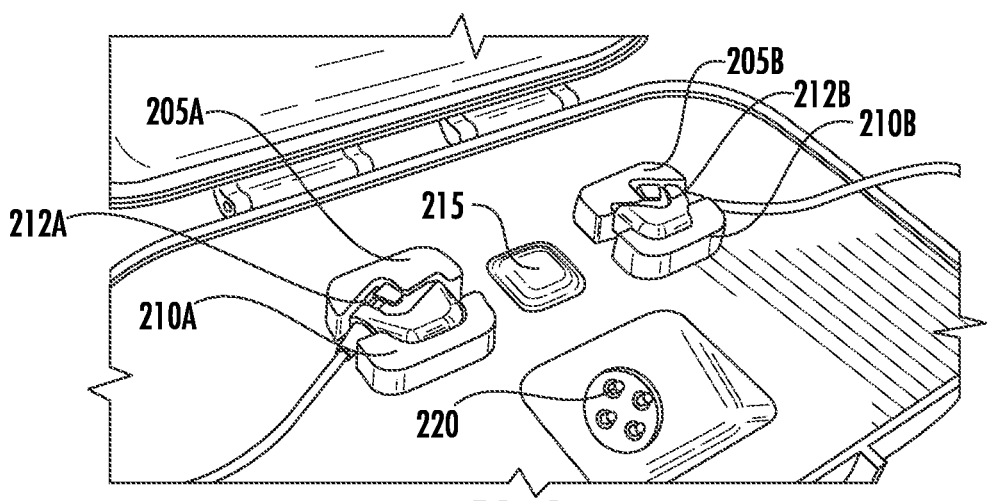
Figure 3D:
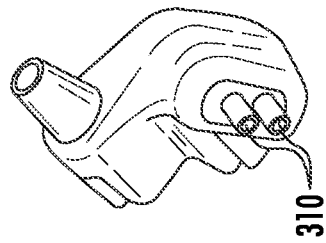
Figure 3C:
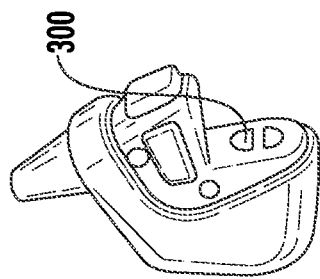
Figure 3B:
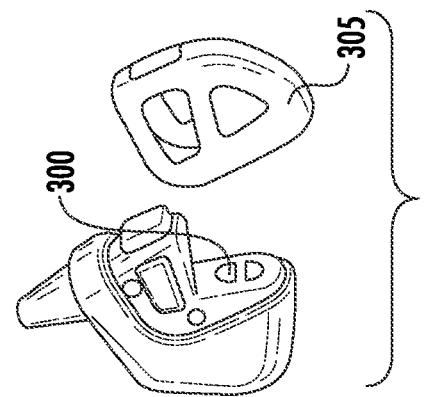
Figure 3A:
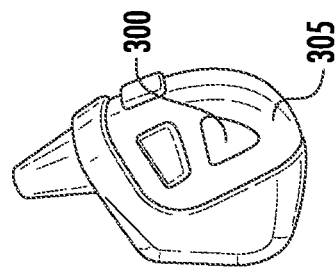
Figure 4A:
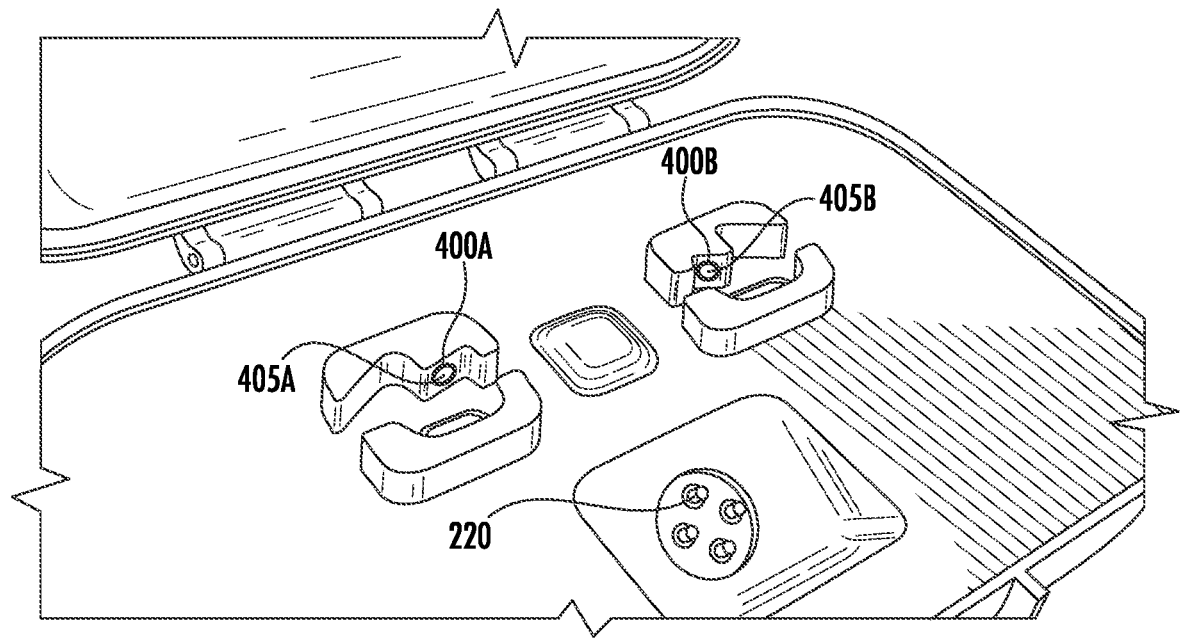
Figure 4B:
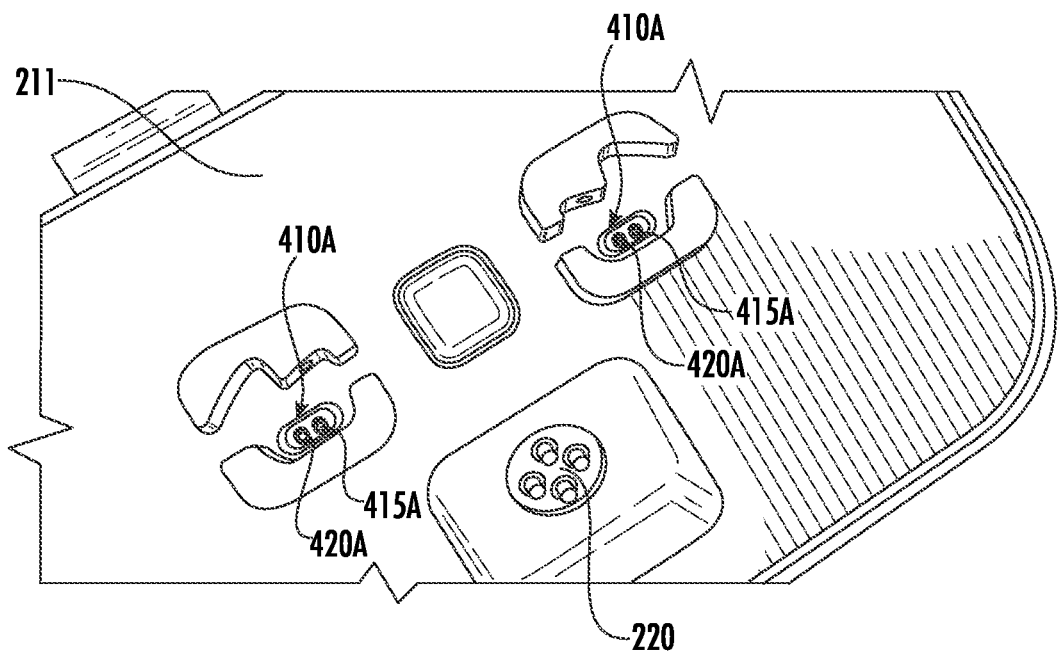
Figure 5A:
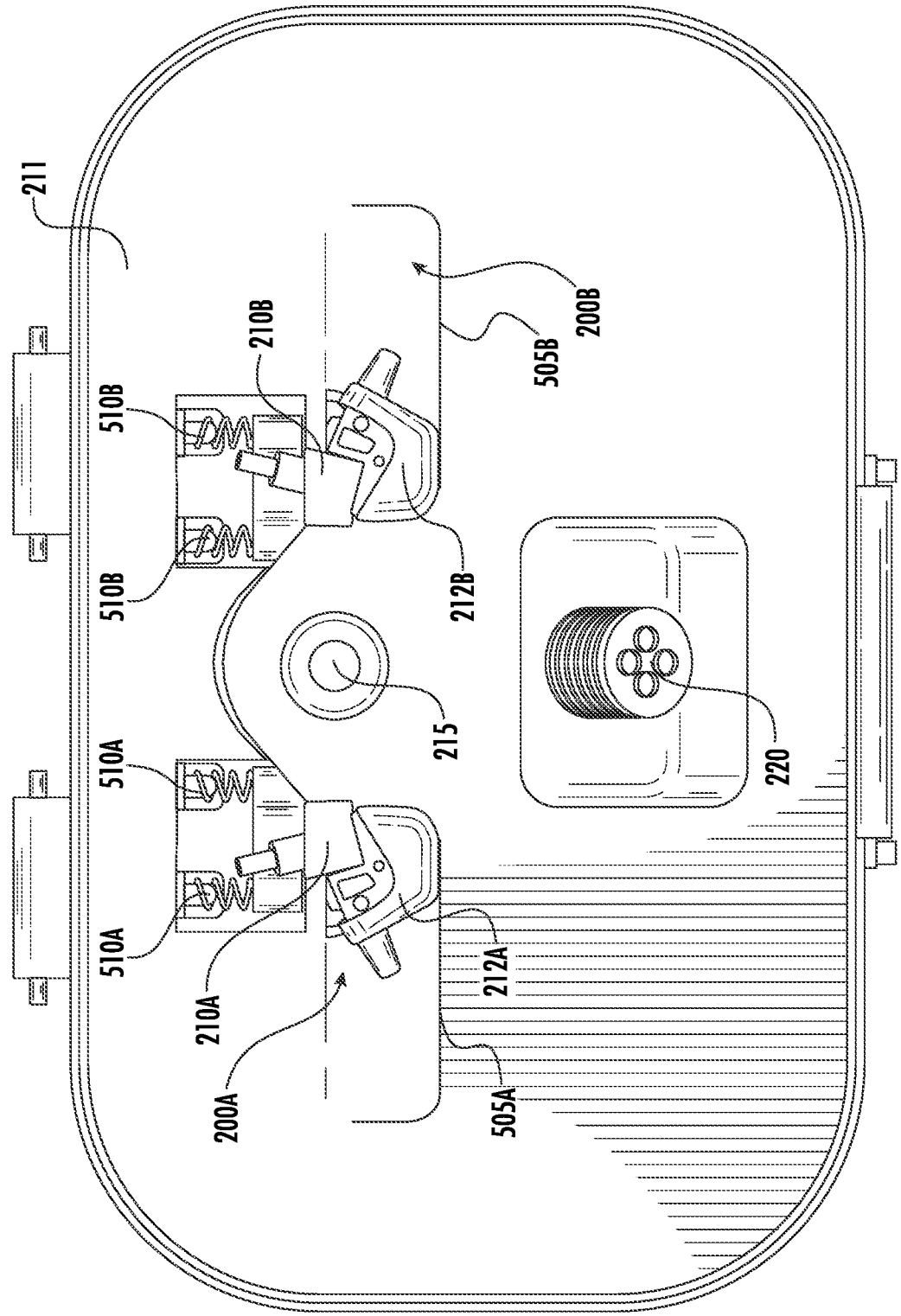
Figure 5B:
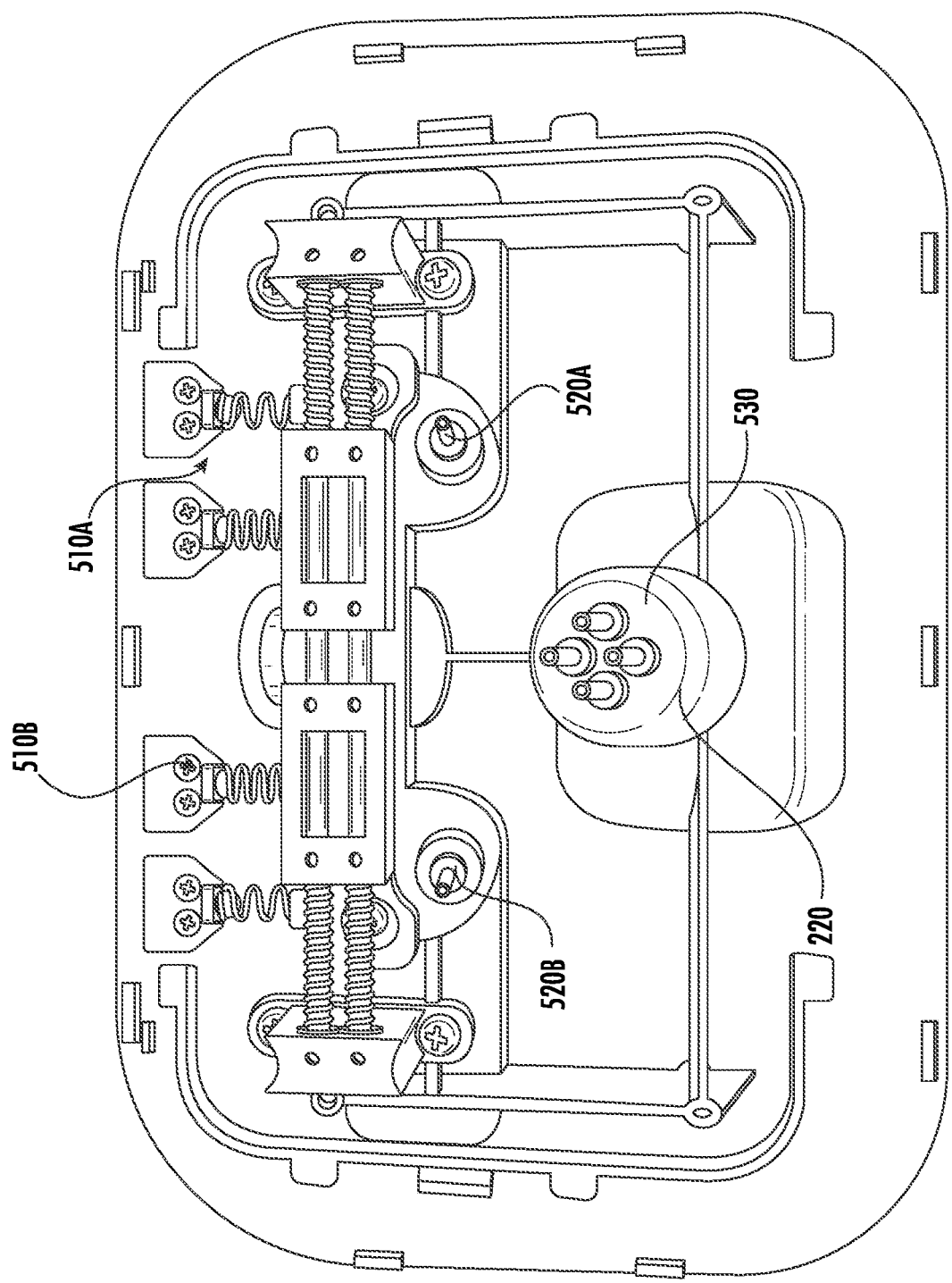
Figure 5C:
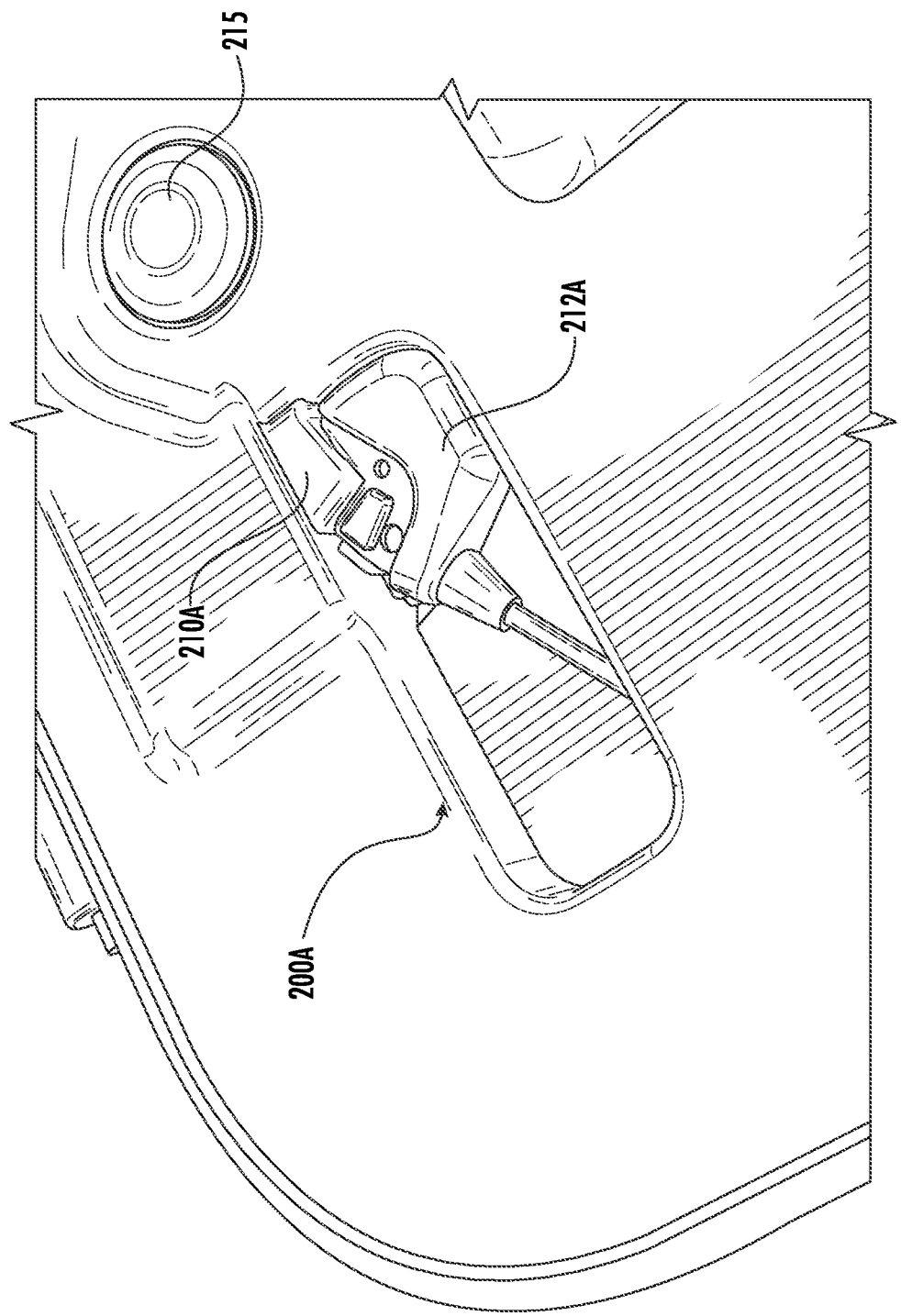
Figure 5D:
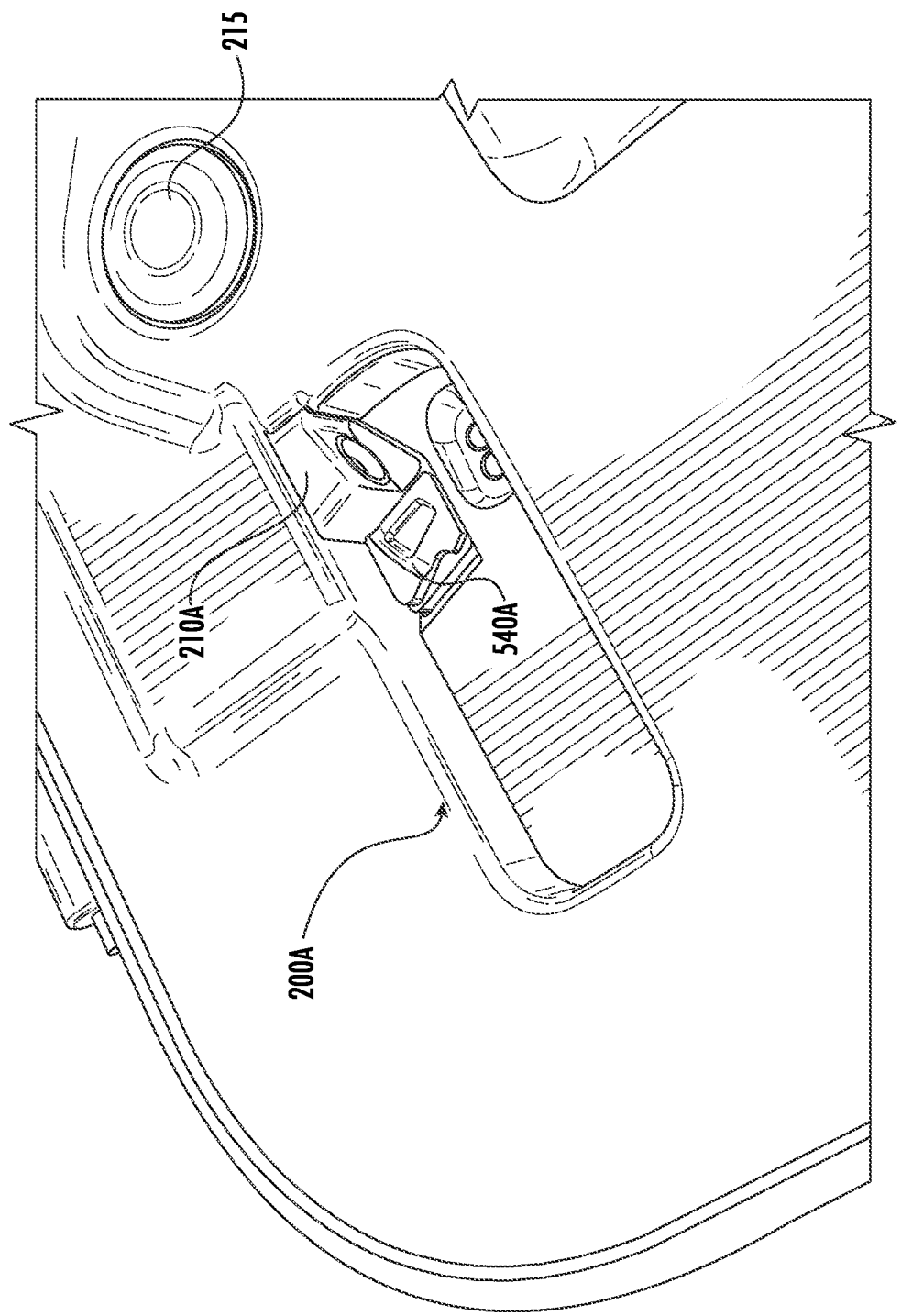
Figure 6:
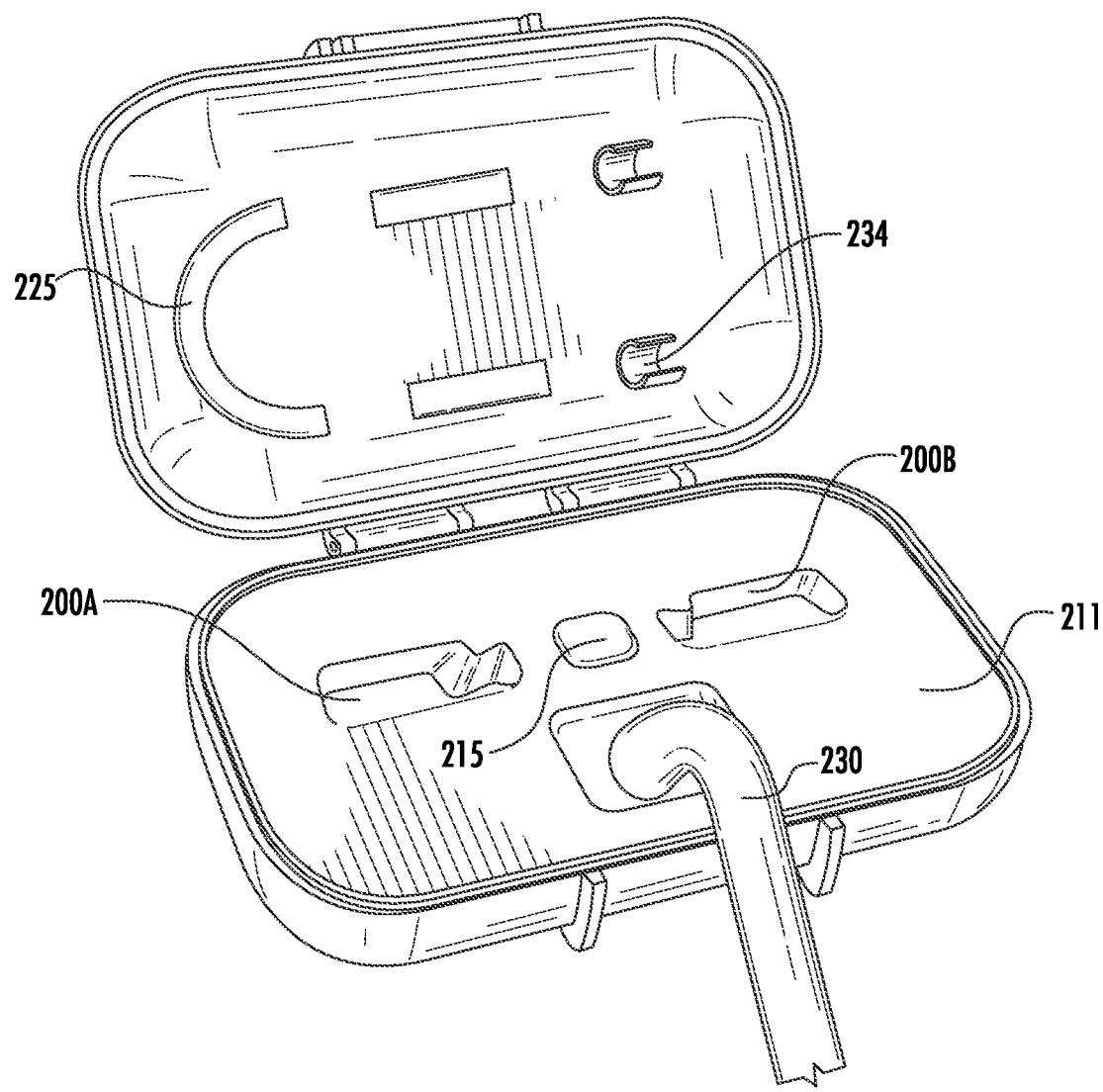

Having thus described certain example embodiments of the present disclosure in general terms, reference will hereinafter be made to the accompanying drawings, which are not necessarily drawn to scale, and wherein:

FIG. 1A is an exterior view of a calibration device in the closed position in accordance with an example embodiment of the present disclosure;

FIG. 1B is an exterior view of the calibration device in the opened position in accordance with an example embodiment of the present disclosure;

FIG. 2A is a calibration device with the lid in the opened position in accordance with an example embodiment of the present disclosure;

FIG. 2B is the calibration device of FIG. 2A with the earpieces positioned within the earpiece receiving mechanisms in accordance with an example embodiment of the present disclosure;

FIGS. 3A-3D are various views of an example earpiece for use in a calibration device in accordance with the present disclosure;

FIGS. 4A and 4B illustrate various example microphone seal locations within earpiece receiving mechanisms in accordance with example embodiments of the present disclosure;

FIG. 5A is another example embodiment of the calibration base in accordance with the present disclosure;

FIG. 5B is a bottom view of the calibration insert in accordance with example embodiments of the present disclosure;

FIG. 5C illustrates an example earpiece positioned within an earpiece receiving mechanism in accordance with example embodiments of the present disclosure;

FIG. 5D illustrates an example ejector mechanism configured to remove an earpiece from the calibration insert in accordance with example embodiments of the present disclosure; and, FIG. 6 illustrates the calibration tubing hooks defined on the lid in accordance with example embodiments of the present disclosure.

DETAILED DESCRIPTION

Some embodiments will now be described more fully hereinafter with reference to the accompanying drawings, in which some, but not all, embodiments are shown. Indeed, various embodiments may be embodied in many different forms and should not be construed as limited to the embodiments set forth herein; rather, these embodiments are provided so that this disclosure will satisfy applicable legal requirements.

The components illustrated in the figures represent components that may or may not be present in various embodiments of the disclosure described herein such that embodiments may include fewer or more components than those shown in the figures while not departing from the scope of the disclosure. Some components may be omitted from one or more figures or shown in dashed line for visibility of the underlying components.

Many hearing devices used in industrial application measure sound using internal and/or external microphones that require calibration. While the initial calibration can be completed during the production of the hearing device, periodic calibration may be useful and/or necessary to maintain the operation of the hearing device. Hearing devices used in industrial applications, such as high noise applications, need a certain level of accuracy in order to provide adequate operating functionality. In some examples and in order to calibrate a hearing device, an air-tight seal needs to be maintained between each internal and external microphone and the calibration device itself. Various embodiments discussed herein allow for a portable calibration device with extended lifetime use due to the configurations discussed herein. Embodiments discussed herein, in some examples, allow for the use of a spring loaded tensioning component to provide additional sealing capabilities beyond a traditional seal. Additionally or alternatively, various example embodiments of the portable calibration device allow for a compact design that, in some examples allows for easy storage and on-site calibration after production without complex systems.

FIG. 1A is an exterior view of a calibration device in an instance in which the calibration device is closed in accordance with an example embodiment of the present disclosure. In various embodiments, the calibration device 10 may be portable and configured to couple to a calibrator system. In various embodiments, the calibrator system may be a sound calibrator. In various embodiments, the calibration system may be a sound source (e.g., a laboratory standard sound source may be used for calibration). In various embodiments, the calibration system may be configured to operate under hostile environment conditions. For example, the calibration system may be a pistonphone (e.g., a pistonphone may operate on the principle of four reciprocating pistons actuated by a precision machined cam with a sinusoidal profile). In various embodiments, the calibrator system may be an exterior system configured to provide air to the microphone to calibrate the earpiece using the airtight seals provided by the calibration device 10 discussed herein. For example, the calibrator system may be a sound calibrator configured to produce a specific sound signal (e.g., a sinusoidal sound signal of 250 hertz or 1000 hertz at 98 dB or 114 dB).

As shown in FIG. 1A, the calibration device 10 may have a calibration base 100 and a calibration lid 105. In various embodiments, the calibration lid 105 may be coupled to the calibration base 100. In various embodiments, the calibration lid 105 may be rotatably attached to the calibration base 100 at the coupling end 115 of the calibration base 100. In various embodiments, the calibration lid 105 may be configured to move between a closed position (FIG. 1A), in which the lid is coupled to the calibration base 100 via the fastening mechanism 110, and an open position (FIG. 1B), in which the fastening mechanism 110 between the calibration base 100 and the calibration lid 105 is decoupled, such that the calibration lid rotates about the coupling end 115 to expose an interior of the calibration base (e.g., a calibration insert 211).

In various embodiments, the calibration device 10 may be configured to lay flat or otherwise rest on a surface in an instance in which the calibration device 10 is in the open position, as shown in FIG. 1B. In various embodiments, the calibration lid 105 may have one or more grooves 107 to, in some examples, provide additional stability to the calibration device 10 in an instance in which the calibration device 10 is in the open position. As discussed below in reference to FIGS. 2A and 2B, in an instance in which the calibration lid 105 is opened (e.g., the fastening mechanism 110 is decoupled), the at least one earpiece receiving mechanism 200A, 200B may be exposed, such that the earpieces may be disposed therein for calibration using the calibration device 10.

In various embodiments, the calibration device 10 may resemble a case in an instance in which the calibration device 10 is in the closed position, such that, in some examples, the calibration device may be portable (e.g., capable of being carried with relative ease). In various embodiments, the calibration base 100 and/or the calibration lid 105 may have a handle to allow the calibration device 10 to be carried by a person. Additionally, in some examples, the closed position of the calibration device 10 may provide a compact device that allows for quick and easy storage (e.g., the calibration device 10 may be stored when not in use). For example, all of the components needed to connect the calibration device 10 to the calibration system may be stored within the calibration device 10 in the closed position. In various embodiments, the calibration lid 105 may be attached to the calibration base 100 in various ways not discussed herein. For example, the calibration device 10 may have multiple fastening mechanisms, such that the calibration lid 105 may be removed from the calibration base 100 completely in an instance in which the calibration device 10 is in the open position.

In various embodiments, the calibration base 100 and/or the calibration lid 105 may define a rounded outer surface, such that an ergonomic shape may, in some examples, be achieved. In various embodiments, the calibration base 100 may have a calibration base edge 101 and the calibration lid 105 may have a calibration lid edge 111. In various embodiments, in an instance in which the calibration device 10 is in the closed positioned, the calibration base edge 101 and the calibration lid edge 111 may engage with one another, such that the interior of the calibration device (discussed in reference to FIG. 2A-2B) may be sealed (e.g., protected from the environment to allow for storage).

FIG. 2A is yet a further view of an example calibration device with the lid in the opened position in accordance with an example embodiment of the present disclosure. In various embodiments, the calibration lid 105 may be configured to store or otherwise retain calibration tubing 230 in an instance in which the calibration tubing 230 is not being used (e.g., not coupled to the calibration tubing receiver 220). In some examples, the calibration tubing 230 may be operable to connect to a calibration device at a first end and a calibration tubing receiver 220 in the calibration insert 211.

As shown in FIGS. 2A and 6, the calibration lid 105 may define an interior compartment 201 within the calibration device 10. In an instance in which the calibration device 10 is in the closed positioned, for example, the interior compartment 201 of the calibration lid 105 may be defined between the interior surface 202 of the calibration lid 105 and the calibration insert 211 of the calibration base 100. In various embodiments, the interior compartment 201 of the calibration lid 105 may define a lid depth defined as the distance between the inner surface 202 and the lid edge 203. In some embodiments, the lid depth may be sufficient to allow the calibration tubing 230 to be housed within the interior compartment 201 in an instance in which the calibration device 10 is in the closed position.

In various embodiments, the interior compartment 201 of the calibration lid 105 may define one or more calibration tubing hooks 225 and/or one or more calibration collars 235 configured to hold the calibration tubing 230 in place during storage. In various embodiments, at least one of the calibration tubing hooks 225 may provide a generally curved shape such that, in some examples, the calibration tubing 230 does not experience stress and/or creases when stored. In various embodiments, one or more calibration collars 235 may be provided to receive (e.g., slideably receive and/or surround) each end of the calibration tubing 230 in an instance in which the calibration tubing 230 is engaged with the calibration tubing hook 225, such as shown in FIG. 2A. In various embodiments and in an instance in which the calibration tubing 230 may be held in place within the calibration lid 105, the calibration lid 105 may capable of being moved from the opened position into the closed positioned.

In some examples, the fastening mechanism 110 may fasten the calibration lid 105 to the calibration base 100). In various embodiments, the lid depth may be sufficient to allow the calibration tubing 230 to be held without interfering with the calibration insert 211 of the calibration base 100 in an instance in which the calibration device 10 is in the closed position.

In various embodiments, the calibration base 100 may comprise a calibration insert 211 configured to fit within and/or otherwise be secured by the calibration base 100. In some alternative embodiments, the calibration insert 211 may be integrally formed with the calibration base 100. In various embodiments, the calibration insert 211 may be a separate component operably coupled within the calibration base 100. In various embodiments in which the calibration insert 211 is a separate component, the calibration insert 211 may be snuggly fit and/or rigidly attached to the calibration base 100 (e.g., the calibration insert 211 may be glued into position).

In various embodiments, the calibration insert 211 may include at least one earpiece receiving mechanism 200A, 200B, a ejector activator 215, and a calibration tubing receiver 220. In various embodiments, the calibration tubing receiver 220 may be configured such that the calibration tubing 230 can be removably could to the calibration tubing receiver 220 at a first end and to a calibration system (not shown) at a second.

As shown, in various embodiments, the calibration insert 211 of the calibration base 100 may include one or more earpiece receiving mechanisms (e.g., a left earpiece receiving mechanism 200A and a right earpiece receiving mechanism 200B), a ejector activator (e.g., ejector button 215), and a calibration tubing receiver 220. In various embodiments, the left earpiece receiving mechanism 200A and the right earpiece receiving mechanism 200B may each include a left stationary block 205A and a right stationary block 205B, respectively, configured to engage with a given earpiece by a force provided by the tensioning component 210A, 210B. In various embodiments, the left earpiece receiving mechanism 200A may be a mirror image of the right earpiece receive mechanism 200B.

In various embodiments, the left earpiece receiving mechanism 200A may be configured to receive an earpiece designed for a user's left ear and the right earpiece receiving mechanism 200B may be configured to receive an earpiece designed for the user's right ear. In some examples, the stationary block 205A, 205B may protrude from the calibration insert 211 surface. In some embodiments, the stationary block 205A, 205B may have a height that is substantially equal to the height of an earpiece and define opposing faces to the given tensioning component 210A, 210B that are etched or otherwise molded into a pattern that is complementary to an earpiece (e.g., a substantially jagged path, a relatively smooth path or the like). In various embodiments, the left stationary block 205A and the right stationary block 205B may be molded as a part of the calibration insert 211. Alternatively, the left stationary block 205A and the right stationary block 205B may be fixably attached to the calibration insert 211 such that the left stationary block 205A and the right stationary block 205B may each remain fixed in relation to the calibration base 100.

In various embodiments, each of the one or more earpiece receiving mechanisms (e.g., left earpiece receiving mechanism 200A and right earpiece receiving mechanism 200B) may also include a tensioning component (e.g., left tensioning component 210A and right tensioning component 210B). In some examples, at least a portion of the tensioning component 210A, 210B may protrude from the calibration insert 211. In various embodiments, the tensioning component 210A, 210B may have a height that this substantially equal to the height of an earpiece and define an opposing face to the given stationary block 205A, 205B that are etched or otherwise molded into a pattern that is complementary to an earpiece (e.g., a substantially jagged path, a relatively smooth path or the like).

The left tensioning component 210A and the right tensioning component 210B may each be spring loaded, such that the respective spring provides a force on the respective tensioning components 210A, 210B in the direction of the respective stationary block 205A, 205B (e.g., the given tensioning component 210A, 210B has a restorative force in the direction of the respective stationary block 205A, 205B, such that the tensioning component 210A, 210B may resist any attempted movement in the direction opposite of the stationary block 205A, 205B). For example, the respective tensioning component 210A, 210B may be moved or otherwise urged away from the respective stationary block 205A, 205B to allow the earpiece 212A, 212B to be placed between the respective tensioning component 210A, 210B and the respective stationary block 205A, 205B. In operation and once user releases the given tensioning component 210A, 210B, the given tensioning component will move in the direction of the respective stationary block 205A, 205B into engagement with the respective earpiece 212A, 212B. In various embodiments, the force provided by the spring loaded tensioning component 210A, 210B may hold the earpieces 212A, 212B in place during calibration. For example, the spring loaded tensioning component 210A, 210B may provide a 1.5N counterforce in various embodiments to hold the earpieces 212A, 212B in place during calibration. In various embodiments, the force provided by the spring loaded tensioning component 210A, 210B may depend on the force needed to hold the earpieces in place during calibration.

Additionally, in various embodiments as discussed in more detail in reference to FIGS. 5A and 5B, the tensioning components 210A, 210B may each be configured to maintain the seal between the microphone seals provided in the earpiece receiving mechanisms 200A, 200B and the earpiece microphones of the given earpieces 212A, 212B. In such embodiments, the seal provides a sealed fluid connection between the earpiece microphone and the interface to connect the calibration adapter. For example, the seal may be a soft material configured to selectively allow sound to pass therethrough. In various embodiments, the tensioning components 210A, 210B may be replaceable, such that the calibration device 10 may be upgraded and/or maintained in working condition.

In various embodiments, the earpiece receiving mechanism 200A, 200B may be specifically designed for a given earpiece design (e.g., the earpiece receiving mechanism 200A, 200B shown in FIGS. 4A and 4B are specifically designed to receive the earpieces shown in FIGS. 3A-3D). In various embodiments, the shape of the given earpiece receiving mechanism 200A, 200B, and the position of the seals may be based on the earpiece to be calibrated. In some embodiments, one or more different earpieces may be calibrated using the same calibration device 10. In various embodiments, one or more of the components may be interchangeable, such that the calibration device may receive a plurality of different shaped earpieces. For example, the earpiece receiving mechanisms 200A, 200B and/or the tensioning components 210A, 210B may be replaced to fit a different earpiece shape. In various embodiments, the microphone seals (e.g., microphone seals 400A, 400B, 410A, 410B) may provide an air-tight sealed connection between the given microphone of the earpiece and the calibration tubing receiver 220 and subsequently the calibration system connected to the calibration tubing receiver 220 via the calibration tubing 230. In various embodiments, the microphone seals (e.g., microphone seals 400A, 400B, 410A, 410B) may be made out of rubber, polyurethane, thermoplastic elastomer, and/or the like. In various embodiments, the force provided on the earpiece by the tensioning component (e.g., tensioning component 210A, 210B) may, in some examples, also provide a sealing force, such that the microphones may be sealed in an instance in which the microphone seals are worn down due to extensive use.

In various embodiments, the calibration base 100 of the calibration device 10 may have a ejector activator (e.g., ejector button 215) configured to allow an earpiece to be ejected from the given earpiece receiving mechanism 200A, 200B. In various embodiments, the ejector button 215 may connected to an ejector mechanism (e.g., the ejector mechanism 540 shown in FIG. 5D), which may cause the given earpiece to be raised (e.g., raised by a few millimeters away from the calibration base 100. In such an embodiment, the raising of the given earpiece may at least partially release the force provided by the given tensioning component 210A, 210B, such that the given tensioning component 210A, 210B disengages from the given earpieces 212A, 212B, such that the earpiece may be removed from the given earpiece receiving mechanism 200A, 200B. In some embodiments, the tensioning component 210A, 210B may be movable by a user independent of the ejector button 215. For example, a user may be able to manually move the given tensioning component 210A, 210B away from the given stationary block 205A, 205B by placing their finger on the tensioning component itself. In various embodiments, one or more different ejector mechanisms may be provided in place of or in addition to the ejector mechanism discussed herein to allow the earpiece to be removed from the calibration device 10.

In various embodiments, the calibration base 100 of the calibration device 10 may have a calibration tubing receiver 220 configured to couple to the calibration tubing 230. In various embodiments, the calibration tubing receiver 220 may be connected to the microphone seals discussed above in reference to FIGS. 4A and 4B. In various embodiments, the type of calibration tubing receiver 220 may be based on the calibration tubing 230 used. For example, the calibration tubing receiver 220 may be configured to receive the end of the calibration tubing 230. In various embodiments, the calibration tubing 230 may connect the calibration device 10 to the calibrator system that is configured to provide the calibration to the sealed microphones within the calibration device. As shown in FIG. 5A, the calibration tubing receiver 220 may have a threading and/or other type of adaptor configured to removably couple the calibration tubing 230 to the calibration device 10. In various embodiments, the at least one earpiece receiving mechanism 200A, 200B and the calibration tubing receiver 220 may be in communication via an air chamber. In various embodiments, an air chamber is positioned between the calibration insert 211 and the calibration base 100. In an example embodiment, the air chamber may be defined between the calibration base 100 and the calibration insert 211 (e.g., the calibration insert 211 and the calibration base 100 may define a sealed compartment). In various embodiments, a dedicated air chamber container may be disposed between the calibration base 100 and the calibration insert 211. In various embodiments, the air chamber may be in communication with the calibration tubing receiver 220 and the earpiece receiving mechanisms 200A, 200B, such that the calibrator system may be coupled to the air chamber and subsequently the earpiece. For example, the air chamber may define any area between the calibration tubing receiver 220 and the earpiece receiving mechanisms 200A, 200B. In various embodiments, in an instance in which an earpiece is engaged in at least one of the earpiece receiving mechanisms 200A, 200B and the calibration system is connected to the calibration device 10 (e.g., via the calibration tubing 230 being coupled with the calibration tubing receiver 220), an air-tight connection may be made between the earpieces and the calibration system.

Referring now to FIGS. 4A and 4B, each of the earpiece receiving mechanisms 200A, 200B may be configured with one or more microphone seals (e.g., microphone seals 400A, 400B, 410A, 410B). In various embodiments, the microphone seal may be provided in the stationary blocks 205A, 205B (e.g., external microphone seal 400A, 400B) and/or the Calibration insert 211 (e.g., internal microphone seal 410A, 410B). In an instance in which the microphone seal is provided in the stationary blocks 205A, 205B, the microphone seal 400A, 400B may take the form of a rubber or metal seal that surrounds one or more seal passageway 405A, 405B defined in the stationary blocks 205A, 205B. In operation and when the earpiece is secured in the earpiece receiving mechanism 200A, 200B, the seal engages the surface of the earpiece (e.g., proximate to the microphone) so as to provide an airtight seal between the earpiece and the seal passageway 405A, 405B, which may not allow sound to escape during calibration. In various embodiments, the microphone seals may provide an air tight connection between the earpiece and an air chamber within the calibration base 100 (e.g., the microphone seal may have an aperture connected to the air chamber within the calibration base 100). In various embodiments, the calibration device 10 may, in some examples, be configured for increased longevity by using both a sealing surface (e.g., the seal of 400A, 400B) and also using the engaging force provided by the tensioning component 210A, 210B. For example, the microphone seals 400A, 400B may deteriorate over time, but the tensioning component 210A, 210B may still provide sufficient force to seal the passageways 405A, 405B between the stationary block 205A, 205B and the given earpiece.

In an instance in which one or more of the microphone seal is provided within the calibration insert 211 (e.g., internal microphone seal 410A, 410B), the microphone seal 410A, 410B may take the form of a rubber or metal seal that surrounds one or more seal passageways 415A, 415B, 420A, 420B defined in the calibration insert 211. In some embodiments, a cavity within the calibration insert 211 may be defined for the internal microphone seals 410A, 410B. In operation and when the earpiece is secured in the earpiece receiving mechanism 200A, 200B, the seal engages the surface of the earpiece (e.g., proximate to the microphone) so as to provide an airtight seal between the earpiece and the seal passageways 415A, 415B, 420A, 420B which may not allow sound to escape during calibration. In various embodiments, the microphone seals may provide an air-tight connection between the earpiece (e.g., the microphone of the earpiece) and an air chamber within the calibration base 100 (e.g., the seal passageways may be a soft material configured to connect the air chamber to the earpiece within the calibration base 100). In various embodiments, the calibration device 10 may, in some examples, be configured for increased longevity by using both a sealing surface (e.g., the seal of 410A, 410B) and also using the engaging force provided by the tensioning component 210A, 210B. For example, the microphone seals 410A, 410B may deteriorate over time, but the tensioning component 210A, 210B may still provide sufficient force to seal the passageways 415A, 415B in part due to the weight of the earpiece.

FIGS. 3A-3D illustrate an example left earpiece 212A for use in the calibration device 10 as discussed herein. In various embodiments, the earpieces 212A, 212B may be configured to at least partially protrude into the ear canal of a user during use (e.g., the earpiece 212A, 212B may be an in-ear headphone). As shown, in various embodiments, the earpieces discussed herein (e.g., left earpiece 212A) may have one or more microphones (e.g., internal and/or external microphones). In various embodiments, the earpiece (e.g., left earpiece 212A shown in FIGS. 3A-3D) may have one or more external microphones 300. In some embodiments, the external microphone(s) 300 may have a removable cover 305 (as shown installed in FIG. 3A and removed in FIG. 3B). In various embodiments, the removable cover 305 may be removed for the calibration process (e.g., the earpiece receiving mechanism may create a seal with the external microphone 300). In various embodiments, the earpiece (e.g., left earpiece 212A shown in FIGS. 3A-3D) may have one or more internal microphones 310. In various embodiments, the internal microphones 310 may also need to be sealed during the calibration process. In various embodiments, each of the microphones on the given earpiece 212A, 212B may need to be sealed to allow for calibration to be effective.

FIGS. 5A and 6 illustrate another example calibration base used in various embodiments of the present disclosure. Unless otherwise stated, the operations of the calibration base 100 of FIGS. 5A and 6 are the same as the calibration base 100 discussed in reference to FIGS. 2A and 2B above. As shown in FIG. 5A, in various embodiments, the left earpiece receiving mechanism 200A may include a left earpiece aperture 505A and a tensioning component 210A. Likewise, in various embodiments, the right earpiece receiving mechanism 200B may include a right earpiece aperture 505B and a tensioning component 210B. In various embodiments, the respective tensioning component 210A, 210B may be spring loaded (e.g., one or more springs 510A, 510B may be attached to the tensioning component 210A, 210B at a first end and the calibration insert 211 at another end, such that as the tensioning component 210A, 210B moves away from the area an earpiece is to be disposed, the spring contracts and provides a resistive force to such movement (e.g., the force of the spring maintains the engagement of the earpiece 212A, 212B and the tensioning component 210A, 210B during operation). In various embodiments, the respective tensioning component 210A, 210B may be configured to protrude into the respective earpiece aperture 505A, 505B, such that the tensioning component 210A, 210B engages with the respective earpiece 212A, 212B to hold the earpiece within the respective earpiece aperture 505A, 505B. In various embodiments, a ejector activator (e.g., ejector button 215) may be provided to disengage one or more tensioning components 210A, 210B from the respective earpiece 212A, 212B by raising the given earpiece 212A, 212B to allow for the earpiece to be removed from the calibration device 10. As shown in FIG. 5A, in various embodiments, the calibration tubing receiver 220 may include a threading to allow the calibration tubing 230 to be removably attached to the calibration base 100. FIG. 6 illustrates the calibration tubing 230 being coupled to the calibration tubing receiver 220 in accordance with various embodiments.

In various embodiments, the calibration device 10 may be operably coupled to a calibration system to calibrate one or more earpieces held within the earpiece receiving mechanisms 200A, 200B. In various embodiments, the calibration tubing 230 may, in operation, be operably coupled to the calibration system at one end and subsequently attached to the calibration tubing receiver 220 of the calibration device 10 at the opposite end of the calibration tubing 230. In various embodiments, the calibration tubing receiver 220 may be in communication with an air chamber that may also be coupled with one or more earpiece receiving mechanisms, such that an air-tight connection may be achieved between one or more microphones of the earpiece 212A, 212B received by the earpiece receiving mechanism 200A, 200B. As discussed above, the calibration system may be a sound source (e.g., a laboratory standard sound source may be used for calibration). In various embodiments, the calibration system may be configured to operate under hostile environment conditions. For example, the calibration system may be a pistonphone (e.g., a pistonphone may operate on the principle of four reciprocating pistons actuated by a precision machined cam with a sinusoidal profile). As such, the calibration device 10 may be operably coupled to the calibration system (e.g., via the calibration tubing 230) that isolates the microphones of the earpieces 212A, 212B installed in the earpiece receiving mechanism 200A, 200B.

As shown in FIG. 5B, each earpiece receiving mechanisms 200A, 200B may have one or more calibration tubing adaptor connectors 520A, 520B configured to connect the given earpiece receiving mechanism 200A, 200B to the calibration tubing receiver 220 (e.g., via connectors 530). For example, the air chamber discussed above may be defined in the tubing connecting the one or more calibration tubing adaptor connectors 520A to the calibration tubing receiver 220. Additionally or alternatively, one or more calibration tubing adaptor connectors 520A, 520B may be operably coupled to an individual air chamber (e.g., an air chamber may be defined between one or more of the calibration tubing adaptor connectors 520A, 520B and the calibration tubing receiver. As shown in FIG. 5B, each earpiece receiving mechanisms 200A, 200B may define one or more springs 510A, 510B, configured to hold the earpiece 212A, 212B in place during calibration (e.g., the spring may hold the given tensioning component 210A, 210B in place during calibration.

Referring now to FIGS. 5C and 5D, the operations of the ejector button 215 are shown in accordance with various embodiments. As shown in FIG. 5C, in an instance an earpiece is positioned with the earpiece receiving mechanism 200A, an ejector button 215 (e.g., a pressable button or the like) may be engageable by a user (e.g., a user may be able to depress the ejector button 215). In various embodiments, the ejector button 215 may be connected to an ejector mechanism 540 within the earpiece receiving mechanism 200A, 200B configured to engage with at least one of the components of the earpiece receiving mechanism 200A, 200B. For example, as shown in FIG. 5D, the ejector mechanism 540 may be configured, upon activation, engage with a given earpiece 212A, 212B, to raise the earpiece away from the calibration insert, such that the force provided by the tensioning component on the earpiece is reduced allowing for the earpiece to be removed. In various embodiments, the ejector mechanism 540 may interact with other components of the earpiece receiving mechanism 200A, 200B to assist the removal of an earpiece from the given earpiece receiving mechanism. In various embodiments, each earpiece receiving mechanism 200A, 200B may have a ejector mechanism 540 activate either by a common or independent ejector buttons. In various embodiments, the ejector button 215 may be any type of activation mechanism.

Many modifications and other embodiments of the disclosure set forth herein will come to mind to one skilled in the art to which the disclosure pertains having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

That which is claimed:

1. A calibration device for a hearing earpiece, the calibration device comprising:
    a calibration base comprising a calibration insert, and,
    at least one earpiece receiving mechanism defined on the calibration insert, the at least one earpiece receiving mechanism configured to calibrate at least one earpiece, wherein the at least one earpiece receiving mechanism is configured to at least partially receive the at least one earpiece, wherein the at least one earpiece receiving mechanism comprises a tensioning component, wherein the tensioning component is spring loaded and is configured to hold the at least one earpiece in the at least one earpiece receiving mechanism during calibration.

2. The calibration device of claim 1, further comprising an air chamber, wherein the air chamber is defined between the calibration base and the calibration insert.

3. The calibration device of claim 2, wherein the at least one earpiece receiving mechanism is configured to create a sealed connection between the at least one earpiece and the air chamber.

4. The calibration device of claim 2, further comprising a calibration tubing receiver configured to operably couple the air chamber with a calibrator system, wherein the calibrator system provides calibration to the at least one earpiece held in the at least one earpiece receiving mechanism.

5. The calibration device of claim 1, wherein the at least one earpiece receiving mechanism comprises one or more microphone seals configured to engage with the at least one earpiece such that an airtight seal is achieved between the one or more microphone seals and at least one microphone of the at least one earpiece.

6. The calibration device of claim 1 further comprising an ejector mechanism, wherein the ejector mechanism is configured to allow for removal of the at least one earpiece from the calibration device.

7. The calibration device of claim 1, wherein the at least one earpiece receiving mechanism comprises a stationary block, such that the at least one earpiece is held in place during operation between the stationary block and the tensioning component.

8. The calibration device of claim 7, wherein the stationary block comprises a microphone seal, wherein the microphone seal is configured to seal at least one microphone of the at least one earpiece in an instance the at least one earpiece is positioned between the stationary block and the tensioning component.

9. The calibration device of claim 7, wherein an interior microphone seal is positioned on the calibration device between the stationary block and the tensioning component, wherein the interior microphone seal is configured to seal another microphone of the at least one earpiece in an instance in which the at least one earpiece is positioned between the stationary block and the tensioning component.

10. The calibration device of claim 1 further comprising a calibration tubing configured to be removably attached to a tubing receiver at a first end and a calibrator system at a second end opposite the first end.

11. The calibration device of claim 9 further comprising a lid, wherein the lid is configured to be removably coupled to the calibration base at a locking end of the calibration base and operably coupled to the calibration base at a connection end opposite the locking end, wherein the lid is configured to move between an opened position and a closed position.

12. A method of manufacturing a calibration device for a hearing earpiece, the method comprising:
    providing a calibration base comprising a calibration insert, and,
    providing at least one earpiece receiving mechanism defined on the calibration insert, the at least one earpiece receiving mechanism configured to calibrate at least one earpiece, wherein the at least one earpiece receiving mechanism is configured to at least partially receive the at least one earpiece, wherein the at least one earpiece receiving mechanism comprises a tensioning component, wherein the tensioning component is spring loaded and is configured to hold the at least one earpiece in the at least one earpiece receiving mechanism during calibration.

13. The method of claim 12, further comprising providing an air chamber, wherein the air chamber is defined between the calibration base and the calibration insert.

14. The method of claim 13, wherein the at least one earpiece receiving mechanism is configured to create a sealed connection between the at least one earpiece and the air chamber.

15. The method of claim 13, further comprising providing a calibration tubing receiver configured to operably couple the air chamber with a calibrator system, wherein the calibrator system provides calibration to the at least one earpiece held in the at least one earpiece receiving mechanism.

16. The method of claim 12, wherein the at least one earpiece receiving mechanism comprises one or more microphone seals configured to engage with the at least one earpiece such that an airtight seal is achieved between the one or more microphone seals and at least one microphone of the at least one earpiece.

17. The method of claim 12 further comprising providing an ejector mechanism, wherein the ejector mechanism is configured to allow for removal of the at least one earpiece from the calibration device.

18. The method of claim 12, wherein the at least one earpiece receiving mechanism comprises a stationary block, such that the at least one earpiece is held in place during operation between the stationary block and the tensioning component.

19. The method of claim 18, wherein the stationary block comprises a microphone seal, wherein the microphone seal is configured to seal at least one microphone of the at least one earpiece in an instance the at least one earpiece is positioned between the stationary block and the tensioning component.

20. The method of claim 19, wherein an interior microphone seal is positioned on the calibration device between the stationary block and the tensioning component, wherein the interior microphone seal is configured to seal another microphone of the at least one earpiece in an instance in which the at least one earpiece is positioned between the stationary block and the tensioning component.

21. The method of claim 12 further comprising providing a calibration tubing configured to be removably attached to a tubing receiver at a first end and a calibrator system at a second end opposite the first end.

22. The method of claim 21 further comprising operably coupling a lid to the calibration base, wherein the lid is configured to be removably coupled to the calibration base at a locking end of the calibration base and operably coupled to the calibration base at a connection end opposite the locking end, wherein the lid is configured to move between an opened position and a closed position.

\* \* \* \* \*